(12) United States Patent
Miura et al.

(10) Patent No.: US 9,666,320 B2
(45) Date of Patent: May 30, 2017

(54) TRITIUM REMOVAL DEVICE FOR LITHIUM LOOP

(75) Inventors: Kuniaki Miura, Hitachi (JP); Tooru Kobayashi, Sennan-gun (JP); Noriyosu Hayashizaki, Tokyo (JP); Nobuo Namiki, Takahagi (JP)

(73) Assignees: Sukegawa Electric Co., Ltd., Hitachi-shi, Ibaraki (JP); Kyoto University, Kyoto-shi, Kyoto (JP); Tokyo Institute of Technology, Tokyo (JP)

( * ) Notice: Subject to any disclaimer, the term of this patent is extended or adjusted under 35 U.S.C. 154(b) by 605 days.

(21) Appl. No.: 13/885,875

(22) PCT Filed: May 24, 2012

(86) PCT No.: PCT/JP2012/063244
§ 371 (c)(1),
(2), (4) Date: Aug. 23, 2013

(87) PCT Pub. No.: WO2013/018421
PCT Pub. Date: Feb. 7, 2013

(65) Prior Publication Data
US 2013/0322587 A1    Dec. 5, 2013

(30) Foreign Application Priority Data
Aug. 4, 2011   (JP) ................................. 2011-170599

(51) Int. Cl.
*G21G 1/10*    (2006.01)
*G21G 1/00*    (2006.01)
(Continued)

(52) U.S. Cl.
CPC ............... *G21G 1/001* (2013.01); *A61N 5/10* (2013.01); *G21B 1/115* (2013.01); *G21K 5/00* (2013.01);
(Continued)

(58) Field of Classification Search
CPC .. G21G 1/00; G21G 1/001; G21G 2001/0094; G21G 1/02; G21G 1/06; G21G 1/08; G21B 1/115
See application file for complete search history.

(56) References Cited

U.S. PATENT DOCUMENTS

| 3,937,649 A * | 2/1976 | Ridgely | ............... G21C 19/303 376/310 |
| 4,532,102 A * | 7/1985 | Cawley | .................... G21G 1/02 376/185 |

(Continued)

FOREIGN PATENT DOCUMENTS
JP    63-305296 A    12/1988

OTHER PUBLICATIONS
Form PCT/ISA/210 International Search Report (English language) date of mailing Aug. 14, 2012 (1 page).
(Continued)

*Primary Examiner* — Marshall O'Connor
(74) *Attorney, Agent, or Firm* — Flynn, Thiel, Boutell & Tanis, P.C.

(57) ABSTRACT

A tritium removal device for a lithium loop contains a neutron source (1) for colliding protons on a lithium flow, thereby generating neutrons, a lithium tank (11) for the lithium passing through this neutron source (1) to flow thereto through a flow passage (9), thereby temporarily accumulating it therein, and a lithium pump (17) for circulating and supplying the lithium of this lithium tank (11) to the neutron source (1) through a supply-side flow passage (9'). The lithium tank (11) and the lithium pump (17), into which hydrogen gas containing tritium therein can be easily collected, are enclosed within a hermetically sealed container (7) including an inactive gas therein, so that even if the hydrogen gas including the tritium therein is leaked into the hermetically sealed container (7), it is removed by a hydrogen isotope removal filter.

7 Claims, 1 Drawing Sheet

(51) Int. Cl.
 *G21B 1/11* (2006.01)
 *G21K 5/08* (2006.01)
 *G21K 5/00* (2006.01)
 *H05H 3/06* (2006.01)
 *H05H 6/00* (2006.01)
 *A61N 5/10* (2006.01)

(52) U.S. Cl.
 CPC ............... *G21K 5/08* (2013.01); *H05H 3/06* (2013.01); *H05H 6/00* (2013.01); *A61N 2005/109* (2013.01)

(56) References Cited

U.S. PATENT DOCUMENTS

| 4,849,155 A | * | 7/1989 | Penzhorn | G21B 1/115 376/146 |
| 2009/0279658 A1 | * | 11/2009 | Leblanc | G21C 1/22 376/360 |

OTHER PUBLICATIONS

Y. Edao et al., "Tritium removal by Y hot trap for purification of IFMIF Li target", Fusion Engineering and Design, Jul. 7, 2009, vol. 85, No. 1, pp. 53-57.

* cited by examiner

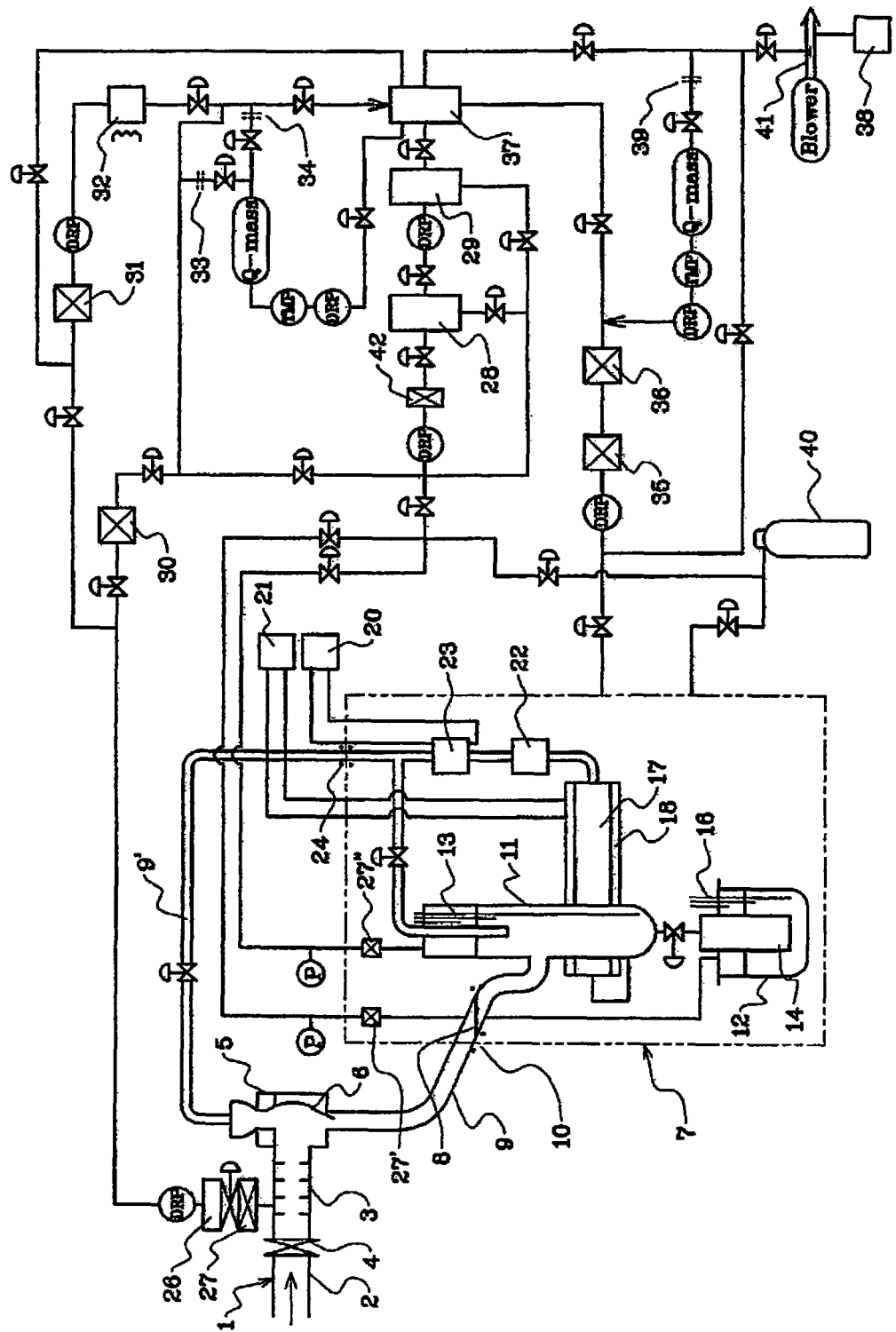

TRITIUM REMOVAL DEVICE FOR LITHIUM LOOP

TECHNICAL FIELD

The present invention relates to a tritium removal device for removing hydrogen and tritium, tritium being an isotopic element of hydrogen, which are generated in a lithium target, to be applied as a neutron source from a lithium loop in which lithium flows circularly, for example, in a boron neutron capture therapy (BNCT), which is applied for the purpose of a cancer medical treatment.

BACKGROUND OF THE INVENTION

The boron neutron capture therapy (BNCT) is a medical treatment achieved for the purpose of selectively killing cancer cells by "α" rays (helium nucleus) and secondary particle radiation of lithium nucleus ($^7$Li), which are generated through neutron capture nuclear reaction from $^{10}$B of a boron isotope ($^{10}$B) compound having a large neutron capture cross section, which is introduced into the cancer cells in advance by irradiating thermal neutrons having a relatively low energy, such as, equal to 0.5 eV or less, upon the cancer cells. Because the range of the "α" rays and so on is very short, only the cells taking $^{10}$B therein are destroyed, and therefore this attracts attention as a medical treatment against the cancer and produces less unfavorable side effects.

In an initial boron neutron capture therapy (BNCT), there are used the neutrons from a nuclear reactor through the deceleration thereof. At present, there are two types, i.e., applying the neutrons which are generated by irradiation of protons accelerated through an accelerator upon solid Be cooled with water- and applying the neutrons which are generated by the irradiation of protons accelerated through an accelerator upon liquid lithium. Herein, explanation will be given on the latter, i.e., the method of applying the neutrons which are generated by irradiating the protons upon the liquid lithium.

The method applying the liquid lithium therein as a target material has advantages that it enables the removal of heat continuously by circulating the lithium and that less fission poison is generated through a nuclear reaction by selecting an irradiating energy equal to no more than 8 MeV. In the present invention, $^7$Li is changed to $^7$Be upon irradiation, but $^7$Be turns back to $^7$Li again after a half-life period of fifty-three (53) days and can be used continuously. Although it is a radioactive material, $^7$Be is enclosed within a lithium loop under the condition of being dissolved in the lithium and it turns back to non-radioactive $^7$Li with an elapse of time. Further, determining the irradiating energy of the protons to be no more than 2.0 MeV brings about an area or region for generating neutrons upon which no deceleration is necessary. Therefore, it is preferable to determine the irradiating energy to this, i.e., equal to no more than 2.0 MeV and also equal to no less than 1.881 MeV threshold value energy, at which the neutrons are generated. This $^7$Be generation in the nuclear reaction depending on the irradiating energy is one over several tens compared to 2.5 MeV, as a source of generating neutrons for use in the boron neutron capture therapy (BNCT), and it is best to apply the protons of this energy band.

In this boron neutron capture therapy (BNCT) is applied a thermal neutron equal to no more than 0.5 eV, which is generated upon the collision of the protons with a lithium target. In this instance, as an example of the reaction in the vicinity of the threshold value at which no moderator is necessary for the neutron, determining the energy of the proton at 2 MeV and current to 20 mA results in that a large thermal energy of 40 kW is given to the lithium. In spite of inputting this large amount of heat therein, it is better for the lithium not to evaporate and, for the purpose of enabling a continuous operation, there are the following necessities. I.e., that the lithium can always pass through a target portion of the neutron source at a high-speed and with a stable thickness, so as to suppress the lithium from increasing in temperature, and that the lithium as the target is always circulated through a lithium loop, which is built to have equipment for removing the heat from lithium in the lithium loop, i.e., a closed loop of lithium. The lithium of the target portion of the neutron source is formed as thin as possible to not disturb the loci of the neutrons generated in the direction of irradiation of the protons, suppressing the attenuation of the neutrons, and further for forming a stable lithium target stream made from a thin laminar flow having a thickness of 0.5 mm, approximately 0.25 mm or greater than that in the depth thereof, into which the protons irradiated, being so-called a "bragg peak", are absorbed abruptly, and then onto this is hit by a ray of protons, thereby generating the neutrons therefrom.

In such a proton source as mentioned above, collision of the protons upon the flow of lithium target generates the neutrons to be applied for the purpose of the medical treatment. Also, at that time, the proton itself turns back to hydrogen by taking an electron of lithium in the periphery thereof and a part of this hydrogen is dissolved into the lithium, but much thereof reacts with the lithium to become lithium hydride. If assuming that the current of the irradiating protons is 20 mA, the amount of hydrogen is only 6.53 g if all of the protons turn back to hydrogen and, if irradiating thereon continuously for one year and assuming that there is 25 Kg of lithium, for example, and that the entirety thereof becomes lithium hydride, then the amount of the lithium hydride obtained is 52.24 g. This reaches only 0.21% of the amount of lithium and is in the condition of being dissolved into the lithium in the form of lithium hydride. On the other hand, the neutrons generated in the lithium upon irradiation of the protons are taken into $^6$Li, i.e., the lithium isotope included in the lithium at 7.4%. Therefore, neutron capture $^6$Li generate tritium, i.e., hydrogen isotope, through the nuclear reaction. The amount of tritium generated upon continuous irradiation of protons for one year is further small, only 2.44 μg, approximately. Nevertheless, the tritium is relatively long in the half-life period thereof, such as 12.3 years. Therefore, it is difficult to discharge this tritium as it is, but rather necessary to remove the tritium, thereby not discharge it into the atmosphere, but it has to be stored or attenuated, if being discharged, in a concentration equal to or lower than a reference value determined according to a law related therewith. A part of this tritium also dissolves into the lithium, similarly, but reacts with the lithium, thereby bringing about tritiated lithium.

In this manner, because the tritium is very low in the quantity thereof and, judging from the amount of hydrogen reacting with the lithium when there is 25 Kg of the lithium, it is in the condition of being dissolved in the lithium in the form of tritiated lithium. Also, hydrated lithium after reacting with the lithium and also the tritiated lithium, are stable at high temperatures. They do not decompose up to 686° C. and therefore is very small in the amount thereof, which is discharged as a gas in a vacuum discharge system or an argon cover gas system.

However, for the tritium generated, since there are cases of it being discharged from the lithium into the vacuum discharge system or the argon cover gas system, even with a very small possibility thereof, with the boron neutron capture therapy (BNCT) mentioned above, it is necessary to remove the radioactive tritium from the lithium loop and not discharge it into the atmosphere. Also, almost all of the hydrogen and the hydrogen isotope generated in a flow of lithium during the time of irradiation become a lithium compound and is hardly decomposable. However, since very little thereof dissolves under the condition of a hydrogen atom, it has a possibility of being gasified in low pressure conditions, etc., for example, that the gas, generated in a flow portion within a vacuum from the target portion up to a quench surface where the pressure is low among flows of the lithium and/or in a quench tank portion, forms bubbles and thereby rises, or that it generates in a vacuum portion of an inlet portion of a pump. The gas generating causes the generation of cavitations in the inlet portion of the pump, or change the flows before and after a nozzle, or brings the flow of lithium to be unstable. Accordingly, also for stably circulating the flow of lithium, there is a necessity of removing the gas of hydrogen and hydrogen isotope.

Conventionally, as the technology for removing the tritium generated from a nuclear power facility, etc., there are already proposed several ones, as described in the following Patent Documents 1 to 4, for example. However, in the conventional arts, no proposal is made of a means for removing the tritium from the lithium loop for such a neutron source as mentioned above. For this reason, in order to propagate such boron neutron capture therapy (BNCT) as mentioned above, widely, in medical facilities, it is desired to develop a lithium target system equipped with a tritium removal device, for enabling the formation of a stable lithium target flow, without diffusing the tritium into the atmosphere, and further to remove the tritium from among the lithium loop, with safety. Also, it is expected to be put in practical use as a target system for use as the neutron source of an accelerator driving type, other than the boron neutron capture therapy (BNCT).

In general, the tritium (T) cannot exist in the form of a tritium molecule where hydrogen exists but almost always exists under the condition of HT, combining with the hydrogen, and it is very hard to separate or divide those from each other, and the characteristics thereof are almost the same too. Therefore, the tritium must be processed together with the hydrogen when trying to remove the tritium from the hydrogen. Among hydrogen isotopes, general hydrogen is called, "light hydrogen", distinguishable from deuterium and tritium, however herein, the light hydrogen is called only by "hydrogen". Also, gasses including the hydrogen and the tritium therein are called, "hydrogen isotope gasses" and, in this device, so as to emphasize or distinguish the tritium, the radioactive material, but always including the light hydrogen therein, it is not called "hydrogen isotope gas", but "tritium" in the case of the removal of the tritium.

PRIOR ART DOCUMENTS

Patent Documents

Patent Document 1 Japanese Patent Laying-Open No. 2005-127718 (2005);
Patent Document 2 Japanese Patent Laying-Open No. Hei 06-331791 (1994);
Patent Document 3 Japanese Patent Laying-Open No. Hei 05-341096 (1993); and
Patent Document 4 Japanese Patent Laying-Open No. Hei 02-93399 (1990).

BRIEF SUMMARY OF THE INVENTION

Problem(s) to be Solved by the Invention

An object of the present invention, accomplished by taking the drawbacks in the tritium removal technologies of the conventional arts as mentioned above into consideration, is to provide a lithium target system, for obtaining a stable lithium, while preventing the gas generated in the lithium from generating cavitations in an inlet of a pump or from generating pulsation or fluid vibration in a valve or a nozzle, by applying a hydrogen and hydrogen isotope removal device for removing the tritium, with safety, without diffusing the hydrogen and the hydrogen isotope, i.e., the tritium, from a lithium group for forming a lithium target flow.

Means for Solving the Problem(s)

The present invention, for accomplishing the object mentioned above, within a lithium loop for flowing lithium circularly, for allowing protons to reach a lithium target portion without colliding on a material, comprises a vacuum pump for maintaining a vacuum while differentially discharging the lithium target portion, and on the discharge side of the vacuum pump, a hydrogen isotope removal filter and a hydrogen storage tank are provided, and has a gas system for accumulating the lithium, including hydrogen and tritium therein, generated in the lithium of the lithium target portion, being a neutron source, so as to keep a necessary NPSH (Net Positive Suction Head) for a pomp input portion due to a head of lithium liquid and, further for decelerating a flow within the tank to let the hydrogen and the tritium gas in the lithium float up and thereby collecting them in an upper portion of the tank for removing gaseous components within the lithium so that no cavitations is generated due to gas, and for sucking the gas including the hydrogen and the tritium collected within the tank. Thereby adjusting the gas pressure, wherein peripheries of equipment where the tritium gas gathers, including a portion of the pump for returning the lithium back to the neutron source, are enclosed in an air-tight hermetically sealed space of an inactive gas atmosphere, such as, argon, etc., and even in case where the tritium leaks out the lithium loop and an argon gas system thereof into this hermetically sealed container, the tritium to be discharged together with a carrier gas from an inside of the hermetically sealed container is removed by a hydrogen isotope removal filter.

Thus, according to the present invention, there is provided a tritium removal device for a lithium loop, comprising: a neutron source 1 for colliding protons with a lithium flow, thereby generating neutrons; a lithium tank 11 for letting the lithium passing through this neutron source 1 to flow through a flow passage 9, forming a quench surface of a lithium flow in the flow passage 9, and for temporarily accumulating it therein, into which an exit of the flow passage forming the quench surface therein is connected, thereby bringing the lithium tank 11 to be applicable with a gas pressure; and a lithium pump 17 for circulating and supplying the lithium of this lithium tank 11 to said neutron source 1 through a supply-side flow passage 9', wherein hydrogen gas containing tritium therein, which is accumulated in a gas system of the lithium loop, is removed by a hydrogen isotope removal filter. Further, said lithium tank 11 and said lithium pump 17 are enclosed within a hermetically sealed container 7 and this hermetically sealed container 7 is connected to a discharge system flow passage through said hydrogen isotope removal filter.

This tritium removal device, being connected hermetically to sealed container 7, encloses all of gasses into which the tritium may leak from the lithium tank 11 and the lithium pump 17 and the gas systems thereof, etc., within the hermetically sealed container 7 including the inactive gas therein, and the gas included in this hermetically sealed container 7 is discharged into the discharge system flow passage passing through the hydrogen isotope removal filter. For this reason, even in cases where the gas leaks out from the lithium tank 11 and the lithium pump 17, etc., it is possible to discharge that gas after removing the tritium contained in the gas.

The amount of tritium contained in the gas of the gas system, from which the tritium gas is removed, i.e., the partial pressure thereof, is measured by a quadrupole mass spectrometer Q-mass accurately by attaching the quadrupole mass spectrometer Q-mass, which is superior in air-tightness, to a connecting tube, after differentially discharging, the gas is diluted with air to be equal to or lower than a reference value depending on the partial pressure, and further is discharged while monitoring the concentration of that diluted by a tritium monitor 38.

When the tritium gas is plentiful, the gas is accumulated in a used-argon tank(s) 28, 29 and/or 37, and the partial pressure thereof is measured, accurately, again, by the quadrupole mass spectrometer Q-mass, and after being choked, a discharge gas is diluted with air to be equal to or lower than the reference value, depending on that partial pressure, and further, the tritium gas in the diluted gas is discharged while monitoring the concentration thereof by the tritium monitor 38.

The lithium tank 11 and the lithium pump 17 and the gas systems thereof, into which the tritium therein can be easily collected, are enclosed within the hermetically sealed container 7 and, also, the gas leaking by any chance, as well as the gas sucked from the gas system for adjustment of gas pressure are removed of the tritium therein through the hydrogen isotope removal filter. Therefore, it never is diffused into the atmosphere, directly.

In the flow passage 9 on the discharge side, reaching from the neutron source 1 to the lithium tank 11 is provided a quench surface for defining a boundary between a gaseous phase on the neutron source 1 side and a liquid phase on the lithium tank 11 side, and the position of the quench surface 8 is maintained by a small pressure within the lithium tank 11. By doing this, it is possible, not only to prevent the lithium flowing from the neutron source 1 into the lithium tank 11 from bringing bubbles into the lithium tank 11, but also to maintain the position of the quench surface 8 within the flow passage 9 to be a little high due to the very low pressure within the lithium tank 11, as well, and bringing NPSH at an inlet of the pump to be high by combining the head of the lithium liquid and the pressure within the lithium tank 11. Thereby enabling the pump to operate with stability and without generating cavitations, even under a reduced pressure.

The flow passages 9 and 9' of the lithium are provided with level gauges 10 and 24, at portions where they penetrate through a wall portion of the hermetically sealed container 7, so as to monitor the existence of lithium in those flow passages 9 and 9' of the lithium. In particular, at a portion of the quench surface 8 mentioned above, which is provided in the flow passage 9 on the discharge side, is provided the level gauge 10 for monitoring the height of that quench surface 8, thereby achieving a stable management.

Effect(s) of the Invention

With the present invention explained above, the tritium removal device removes, in particular, when the tritium leaks from the lithium loop or an argon gas system of a cover gas by any chance, the tritium gas, i.e., the hydrogen and the hydrogen isotope, generated in the lithium flow upon the irradiation of protons, and since the lithium target portion of the neutron source 1 is managed under a vacuum, it is possible to suppress the generation of gas cavitations due to the gas, even under the condition where NPSH is low in the inlet portion of the pump, and the quench surface is provided within a flow passage 9, further so as to retard the flow velocity of the lower lithium within the lithium tank 11 so that the gas can float up to the surface to be taken out from the argon gas in an upper portion of a lithium tank 11. In other words, it is possible to discharge that gas, after removing the tritium included in the gas when the tritium leaks out from the lithium tank 11 and the lithium pump 17, etc., i.e., places where the tritium gas is rich, and therefore the tritium can be supplied circularly, safely and stability, i.e., preventing the tritium included in the lithium discharged from the neutron source 1, from leaking outside.

BRIEF DESCRIPTION OF VIEW OF THE DRAWING

FIG. 1 is a system view of a lithium loop equipped with a tritium removal device.

EMBODIMENT(S) FOR CARRYING OUT THE INVENTION

In accordance with the present invention, a portion including a lithium tank 11 for storing lithium discharged from a neutron source and also a pump for returning the lithium from this lithium tank 11 back to the neutron source 1 are confined within an air-tight enclosed space of an inactive gas, such as argon, etc., for example, wherein tritium accumulating in a gas system of a lithium loop is removed by a tritium removal filter, and further, even when the tritium leaks out from the periphery of the lithium tank and/or the pump where hydrogen isotopes including the tritium can easily come together, the tritium to be discharged from an inside of this hermetically sealed container is removed by the tritium removal filter, thereby accomplishing the object mentioned above.

Hereinafter, a detailed explanation will be made about the best mode for carrying out the present invention by referring to an embodiment.

As is shown in FIG. 1, the neutron source 1 for generating neutrons is sectioned into an accelerator 2 for accelerating protons and a neutron-generating chamber 5 for generating neutrons therein, through a gate valve 4. The former, i.e., the accelerator 2 is decompressed down to vacuum of $1 \times 10^{-5}$ Pa, approximately, although essentially it is desirable to bring also the neutron-generating chamber 5 into a high-vacuum condition, so that no proton accelerated collides with the gas. However, since the high-vacuum also accelerates the evaporation of the lithium, it is necessary to maintain the vacuum at about the vapor pressure of the lithium, such as, $1 \times 10^{-3}$ Pa, approximately, and therefore it is necessary to create a pressure difference of two digits in a short distance between the accelerator 2 and the neutron-generating chamber 5. Thus, they are connected through a proton passage tube 3 provided with an operating discharge orifice for building up the pressure difference from the gate valve 4 to the neutron-generating chamber 5. This proton passage tube 3 is decompressed in the pressure thereof, by a lithium vapor trap 27 filled with wire nets for capturing the lithium vapor therein, a turbo molecule pump 26 and a dry pump DRP.

To a discharge side of this dry pump DRP are connected the turbo molecule pump TMP and the dry pump DRP, via a hydrogen isotope filter made of a hydrogen storage alloy such as Mg—Ni, etc., a valve, and a quadrupole mass spectrometer Q-mass. An orifice is provided between the valves in front of the quadrupole mass spectrometer Q-mass so that they discharge differentially, thereby obtaining the pressure under which the quadrupole mass spectrometer Q-mass can operate. By means of this quadrupole mass spectrometer Q-mass, confirmation is made on a condition of the removal of tritium after the hydrogen isotope filter, and the gas sucked by the turbo molecule pump 26 and the dry pump DRP through the lithium vapor trap 27, after having the hydrogen/hydrogen isotopes removed therefrom through a hydrogen isotope filter 30 made of a hydrogen storage alloy such as Mg—Ni, etc., is measured for hydrogen partial pressure by the quadrupole mass spectrometer Q-mass and is discharged by the dry pump DRP into a used-argon tank 37 or 28, while another part of the gas is discharged through the orifice 33 and other remaining gases into the used-argon tank 37. When the used-argon tank 28 is filled, then the gas is discharged into another used-argon tank 29 by the dry pump DRP.

Also, in this gas flow passage system is provided a bypass passage, but this flow passage system is a route to be used when air comes into the system due to the maintenance of a lithium loop and/or a vacuum pump, etc., wherein suction is made by the turbo molecule pump 26 and the dry pump DRP from the proton passage tube 3 mentioned above through the lithium vapor trap 27. In this flow passage system, the dry pump DRP is connected through a hydrogen/oxygen storage alloy built-in filter 31, receiving a hydrogen/oxygen storage alloy such as Mg—Ni/Mg, etc., therein, in the place of such a filter receiving the hydrogen storage alloy therein, as was mentioned above. When the air is mixed with the gas, which is sucked by the turbo molecule pump 26 and the dry pump DRP from the proton passage tube 3 through the lithium vapor trap 27, this gas is sucked by the dry pump DRP through the hydrogen/oxygen storage alloy built-in filter 31. Further, after removing the hydrogen, the oxygen and nitrogen therefrom, passing through a hydrogen-cum-nitrogen trap 32, which contains a vanadium alloy, etc., therein, and is attached with a heater on an outside thereof, the remaining gas is discharged into the used-argon tank 37. This flow passage system has such a structure that it operates to discharge the gas after passing through the nitrogen trap 32 through an orifice 34, and there is also prepared a bypass passage for sending the gas to the side of the quadrupole mass spectrometer Q-mass mentioned above. Switching of both those passages are conducted through a valve operation.

In the neutron-generating chamber 5 is provided a rectifier plate 6 for forming a thin lithium target flow, and to this rectifier plate 6 is always continuously supplied the lithium. Therefore, a lithium target flow of a thin laminar flow of lithium is formed on the surface thereof. By letting the protons accelerated by the accelerator 2 collide upon the thin lithium target flow on the surface of this rectifier plate 6, neutrons are generated in a direction of the collision. In the boron neutron capture therapy (BNCT), a cancer treatment is performed by using the neutrons having such a direction. Almost all of the protons take electrons in the periphery thereof in this neutron-generating chamber 5, thereby becoming hydrogen and, further, tritium, i.e. the hydrogen isotope, is generated from $^6$Li.

After the collision of protons on the lithium target flow on the rectifier plate 6 mentioned above, the lithium forming the lithium target flow is sent to the lithium tank 11 passing through a lithium flow passage 9 provided on a discharge side. The amount of lithium in the lithium tank 11 is monitored by a level gauge 13 and, within the same lithium tank, is always stocked an approximately certain amount of lithium.

To a bottom portion of the lithium tank 11 is connected a drain tank 12 through valves and a dipping-type electromagnetic pump 14. The lithium within this drain tank 12 is monitored by a level gauge 16. When the lithium in the drain tank 12 is in surplus, it is discharged into the drain tank 12 through an operation of the valve mentioned above, and also, when the lithium in the lithium tank 11 is in shortage for maintaining a desired liquid level, it is pumped up to the lithium tank 11 through driving of the dipping-type electromagnetic pump 14 mentioned above.

With the lithium tank 11 and the drain tank 12 mentioned above are connected an argon gas supply system and the dry pump DRP through lithium vapor traps 27' and 27", each being made up by filling metal nets in a container for removing the lithium vapor, wherein the lithium tank 11 and drain tank 12 are maintained under a very little absolute pressure, such as about 1 kPa, for example. This pressure of 1 kPa corresponds to the pressure of a liquid head (i.e., height) of about 200 mm of lithium. This pressure is monitored by a pressure gauge P.

When operating, a gas system including the lithium tank 11 and the drain tank 12 is brought into a gas communicating condition to have the same pressure, and when an emergency occurs, the valve between the lithium tank 11 and the drain tank 12 is opened so that the lithium within the lithium tank can be drained quickly, through a free fall flow. The reason that the lithium tank 11 and the drain tank 12 to be under a vacuum, other than the neutron-generating chamber 5, are brought into the absolute pressure, such as about 1 kPa, lies in that the lithium and/or the argon gas will not discharge into the atmosphere directly, even if it/they leak(s), since the pressure thereof is lower than that of the atmosphere, and further, for the purpose of suppressing the discharge of the hydrogen from the lithium and the tritium gas under the pressure of argon gas within the lithium loop, down to the smallest, to enclose the tritium gas within the lithium, as much as possible therein, when executing the draining quickly, and thereby to increase the safety when executing the draining quickly. When executing the draining quickly, also the accelerator is instantaneously stopped, automatically, and the gate valve 4 of the neutron-generating chamber 5 in the lithium loop is also instantaneously stopped, thereby to separate the lithium loop, having a very little possibility of producing the radioactive material therein. However, since the gate valve 4 is large and it takes about 1 second to be completely closed, and since it is necessary to let the argon gas permeate through the neutron-generating chamber 5, firstly, after the lithium is lowered down a hot water surface thereof by a certain degree during the time when the emergency draining of lithium is executed, for the purpose of maintaining the vacuum of the accelerator and thereby accelerating re-starting of the accelerator, then the lithium flow passage 9 is connected to a lower side portion of the lithium tank 11 so that argon gas of 1 kPa can be supplied to the neutron-generating chamber 5 firstly when the lithium goes down to this connecting portion, and thereby allow the gate valve 4 to take the time unit of 1 second for the closing thereof. Although not shown in the FIGURE, inserting the lithium flow passage 9 into the lithium tank 11 from an upper flange surface thereof, i.e., a so-called dual-tube type, also brings about the similar effect to that. However, the dual tube makes the diameter of the lithium tank large and a liquid-level gauge must be inserted into a ring-like portion of the dual tube for the purpose of measuring the lithium surface in the lithium tank 11, but because the lithium has a large surface tension, the liquid surface of the lithium is absorbed upwards in a narrow region and this increases an error. Therefore, the ring-like portion, into which the liquid-level gauge should be inserted, must be widened considerably. This further brings the diameter of the lithium tank 11 to be larger, as well as bringing about an increase of the amount or volume of the lithium, being a hazardous material, which is not such a preferable method and, therefore, as is shown in FIG. 1, it is necessary to select the structure of dividing the flow passage 9 the lithium tank 11 from each other, and explanation will be given on it with priority.

In the example shown in the FIGURE, dry pumps DRP are connected on two stages, in series, and to each dry pump DRP on a back side thereof are connected the first used-argon tank 28 and the second used-argon tank 29, wherein the hydrogen isotope gas discharged from the gas system, including the lithium tank 11 and the drain tank 12, is sent to a hydrogen isotope filter 42 by the dry pump DRP, and after removing the hydrogen isotope gas therefrom, it is accumulated within the argon tank 28 and, further, if the used-argon gas tank 20 is filled up, then it is accumulated in the used-argon gas tank 29 through discharge by the dry pump DRP.

Also, the gas accumulated in the used-argon tank 29, finally, is measured for the hydrogen partial pressure thereof by the quadrupole mass spectrometer Q-mass, being differentially discharged from the used-argon tank 37 through the orifice 39, and the gas of the used-argon tank 37 is diluted with air by means of a blower, so that it comes to be equal to or less than a reference value depending on the tritium partial pressure thereof and, further, is discharged while monitoring the diluted concentration thereof by a tritium monitor 38.

Through adjustment of the argon gas pressure by the argon gas supply system and the dry pump DRP mentioned above, the liquid level of the lithium within the lithium tank 11 is maintained at a desired height. The lithium flow passage 9 reaching from the neutron-generating chamber 5 to the lithium tank 11 is connected to the lithium tank 11 at the position in the middle thereof, being lower than the liquid level of the lithium in the lithium tank 11, so that a liquid surface is maintained, dividing a gaseous phase in an upper side and a liquid phase in a lower side on the way of the lithium flow passage, as well as the quench surface 8. The fact that this quench surface 8 is positioned on a side of the lithium flow passage 9 other than the lithium tank 11 and also the height thereof brings about a function of preventing bubbles of the hydrogen gas, including the tritium therein, from being brought into the lithium tank 11 by the lithium flowing from the neutron source 1 into the lithium tank 11.

To the lithium tank 11 is also connected the lithium pump 17, being made of an induction electromagnetic pump. The lithium in the lithium tank 11 is circulated and supplied to a side of the rectifier plate 6 of the neutron-generating chamber 5 mentioned above, passing through the lithium flow passage 9' on the supply side, with driving by this lithium pump 17. In the lithium flow passage 9' on the supply side is provided an electromagnetic flow meter 22 so that the flow amount of the lithium passing through the lithium flow passage 9' on the supply side is measured.

Also, heat exchangers 18 and 23 are provided on the lithium pump 17 and the lithium flow passage 9' on the supply side mentioned above, respectively, wherein the heat exchanger 18 cools or heats the lithium pump 17, while heat exchanger 23 cools or heats the lithium flow passage 9' on the supply side, thereby achieving an adjustment at the desired temperature. This lithium, which is adjusted in the temperature thereof, is supplied to the side of the rectifier plate 6 of the neutron-generating chamber 5 mentioned above through the valves. The heat exchangers 18 and 23 for the lithium pump 17 and the lithium flow passage 9' on the supply side are cooled or heated, respectively, by cooler/heaters 20 and 21, each applying a heating medium therein, being heat-resistant against 350° C., thereby being maintained at the desired temperatures.

The lithium tank 11, the drain tank 12, the lithium pump 17 and the electromagnetic flow meter 22 mentioned above are enclosed within a hermetically sealed container 7, including the exchangers 18 and 23 for the lithium pump 17 and the lithium flow passage 9' therein. To this hermetically sealed container 7 is connected the dry pump DRP, so that it is maintained to be at a negative pressure with respect to the atmosphere. Also, with this hermetically sealed container 7 is connected an argon supply tank 40 through the valves, and with the argon gas being sent out from this argon supply tank 40 to the hermetically sealed container 7, an inside of the hermetically sealed container 7 is maintained at an inactive gas atmosphere.

The gas discharged from the same hermetically sealed container 7 by the dry pump DRP, for decompressing the hermetically sealed container 7, is removed of hydrogen, oxygen and nitrogen, by passing through the filter 35 made of the hydrogen/oxygen storage alloy, such as Mg—Ni/Mg, etc., and also the nitrogen trap 36 made of the vanadium alloy, as the hydrogen isotope removal filter, and thereafter, the remaining gas is discharged into the used-argon tank 37. This system is attached for the purpose of processing the tritium if it leaks out from the lithium and the argon gas system into the hermetically sealed container 7. In the case of discharging the gas from the used-argon tank 37, the hydrogen partial pressure is measured by the quadrupole mass spectrometer Q-mass, and the gas in the used-argon tank 37 is diluted with the air by the blower, depending on the tritium partial pressure thereof, so that it comes to be equal to or less than a reference value and, further, the gas is discharged while monitoring the diluted concentration thereof.

The gas discharged into the inside of this used-argon tank 37 is measured for the tritium partial pressure by the quadrupole mass spectrometer Q-mass, the gas therein being differentially discharged through the orifice 39 and, if the tritium partial pressure is high, the gas is returned from the used-argon discharge tank 37 through a return pipe back to the dry pump DRP, and it also circulates around the hydrogen isotope filter 35 and the nitrogen trap 36. Thereby after being removed of the tritium therefrom, it is returned back to the used-argon discharge tank 37. Thereafter, it is discharged operationally through the orifice 39 and, as a result of measurement by the quadrupole mass spectrometer Q-mass, if the tritium partial pressure of the gas discharged into the used-argon discharge tank 37 is low, then the valve is opened to send the gas into a duct 41, wherein the gas is diluted with a large amount of air sent by the blower into the duct 41 to be equal to or lower than a reference in the concentration thereof, and is discharged into the atmosphere. The tritium concentration of this discharge gas is monitored by the tritium monitor.

Within the tritium removal device for the lithium loop having the structure as mentioned above, hydrogen gas including tritium therein, which is accumulated in the gas system for the lithium loop, is removed by the hydrogen isotope removal filter, and also the gas leaking out from the lithium tank 11 and the lithium pump 17, etc., where the hydrogen gas including the tritium therein can be easily accumulated, is held within the hermetically sealed container, and after removing the tritium included in the gas within this hermetically sealed container, the gas is diluted and further discharged into the atmosphere while monitoring it by the tritium monitor 38. Therefore, a very small amount of the tritium contained in the lithium discharged from the neutron source 1 is removed by the hydrogen isotope removal filter and, further, the partial pressure thereof is measured by the quadrupole mass spectrometer Q-mass. Thereafter, it is diluted with the air by means of the blower, to be discharged while monitoring that the partial pressure thereof is equal to or lower than the reference, by the tritium monitor 38, i.e., it is possible to supply the lithium circularly while preventing the tritium from being leaked directly to the outside.

USABILITY IN INDUSTRY

The present invention can be applied as a tritium removal device for removing tritium, a hydrogen isotope element generated in a lithium target to be a neutron source, from a lithium loop distributing the lithium, cyclically, in the in boron neutron capture therapy (BNCT), which can be applied for the purpose of a cancer medical treatment, for example.

EXPLANATION OF MARKS

1 . . . neutron source
7 . . . hermetically sealed container
8 . . . quench surface
9 . . . flow passage of lithium
9' . . . flow passage of lithium
11 . . . lithium tank
35 . . . filter

What is claimed is:

1. A tritium removal device comprising a lithium loop, the lithium loop comprising a neutron source for generating neutrons through the collision of proton rays with flowing lithium, a lithium tank for storing lithium therein, a first flow passage for transporting lithium from the neutron source to the lithium tank, a second flow passage, a lithium pump for transporting lithium from the lithium tank to the neutron source through the second flow passage and a hermetically sealed container enclosing the lithium tank and lithium pump therein, and the tritium removal device further comprising an argon supply tank for supplying argon gas to the hermetically sealed container, a used argon tank for receiving argon gas from the hermetically sealed container and a hydrogen isotope removal filter for removing tritium-containing hydrogen gas from the argon gas being received in the used argon tank.

2. The tritium removal device of claim 1, additionally comprising a quadrupole mass spectrometer for measuring the partial pressure of the tritium in the argon gas passing through the hydrogen isotope removal filter and a blower for diluting the argon gas passing through the hydrogen isotope removal filter with air so that the measured partial pressure of tritium is at or lower than a reference value.

3. The tritium removal device of claim 1, additionally comprising a quadrupole mass spectrometer for measuring the partial pressure of tritium in argon gas discharged from the used argon tank and a blower for diluting the argon gas discharged from the used argon tank with air so that the measured partial pressure of tritium is at or lower than a reference value.

4. The tritium removal device of claim 2, additionally comprising a tritium monitor for monitoring the concentration of tritium in the diluted argon gas.

5. The tritium removal device of claim 1, additionally comprising a quench surface defining a boundary between a gaseous phase of a neutron source side and a liquid phase of a lithium tank side in the first flow passage.

6. The tritium removal device of claim 5, wherein the position of the quench surface in the first flow passage is held through the pressure of the lithium tank.

7. The tritium removal device of claim 1, additionally comprising level gauges for monitoring lithium in the first and second flow passages at positions where the flow passages penetrate through a wall of the hermetically sealed container.

* * * * *